United States Patent [19]

Bernhart et al.

[11] Patent Number: 4,542,134
[45] Date of Patent: Sep. 17, 1985

[54] DERIVATIVES OF γ-BUTYROLACTONE WITH AN ANTI-ARRYTHMIC ACTIVITY AND COMPOSITIONS

[75] Inventors: Claude Bernhart, Saint Gely du Fesc; Werner Cautreels, Castelnau le Lez; Patrick Gautier, Cournonterral, all of France

[73] Assignee: SANOFI, Paris, France

[21] Appl. No.: 543,898

[22] Filed: Oct. 20, 1983

[30] Foreign Application Priority Data

Nov. 8, 1982 [FR] France .................. 82 18705

[51] Int. Cl.⁴ ............... A61K 31/44; A61K 31/535; C07D 405/04; C07D 413/14
[52] U.S. Cl. .................. 514/236; 514/278; 514/318; 514/336; 514/338; 544/70; 544/131; 546/15; 546/193; 546/283; 546/269
[58] Field of Search ........... 544/70, 131; 546/269, 546/283, 15, 193; 424/248.55, 263, 267

[56] References Cited

U.S. PATENT DOCUMENTS 3,781,295 12/1973 Sutton .................. 546/283

FOREIGN PATENT DOCUMENTS 0027412 4/1981 European Pat. Off. .

OTHER PUBLICATIONS

Chemisch Berichte, vol. 114, No. 1, Jan. 9, 1981, Verlag Chemie, GmbH, Weinheim, pp. 32-48.

Primary Examiner—Robert W. Ramsuer
Attorney, Agent, or Firm—Bacon & Thomas

[57] ABSTRACT

The present invention relates to the products of general formula:

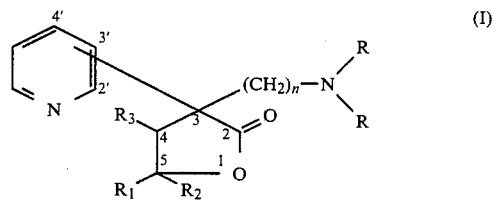

in which:
R represents a straight or branched alkyl group having from 2 to 5 atoms of carbon, or the group

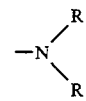

represents a morpholino or piperidino group possibly substituted by 1 or 2 methyl groups;
n=2 or 3;
$R_1$ and $R_2$ considered independently each represent hydrogen or a lower alkyl group (1 to 4 carbon atoms) or $R_1$ and $R_2$ taken together represent a $(CH_2)_m$ group where m=4 or 5, $R_3$ being equal to H or $R_1$ is H and $R_2$ and $R_3$ considered together represent $(CH_2)_p$ where p is 3 or 4
the butyrolactone cycle substitutes the pyridyl group in 2', 3' or 4' position, the salts, isomers and mixtures of isomers of said products; and to a process for preparing said products and to the myocardium-protecting drugs containing same.

11 Claims, No Drawings

DERIVATIVES OF γ-BUTYROLACTONE WITH AN ANTI-ARRYTHMIC ACTIVITY AND COMPOSITIONS

The present invention relates as new industrial products to derivatives of γ-butyrolactone as well as to the methods for preparing them and to the application thereof to therapeutics.

The novel compounds according to the invention respond to the following general formula:

(I)

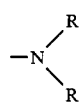

in which:

R represents a straight or branched alkyl group having from 2 to 5 atoms of carbon,
or the group $$-N\begin{matrix}R\\R\end{matrix}$$

represents a morpholino or piperidino group possibly substituted by 1 to 4 methyl groups;

n=2 or 3;

R₁ and R₂ considered independently each represent hydrogen or a lower alkyl group (1 to 4 carbon atoms) or R₁ and R₂ taken together represent a $(CH_2)_m$ group where m=4 or 5; in these two cases R₃ being equal to H or R₁ is H and R₂ and R₃ considered together represent $(CH_2)_p$ where p is 3 or 4 the butyrolactone cycle substitutes the pyridyl group in 2', 3' or 4' position.

Compounds (I) furnish with the inorganic or organic acids soluble salts. These salts, with pharmaceutically acceptable acids, form an integral part of the invention.

Compounds (I) always have an assymmetrical carbon atom, namely atom 3 of the γ-butyrolactone cycle. If substituents R₁ and R₂ are different, the carbon atom 5 which carries them is also an asymmetrical carbon atom. Consequently, compounds (I) may exist in the form of diastereoisomers and optical isomers. These isomers as well as the mixtures thereof form part of the invention.

The compounds of the invention where R₃ is H are obtained from a pyridylacetonitrile in accordance with the reaction diagram indicated hereinafter:

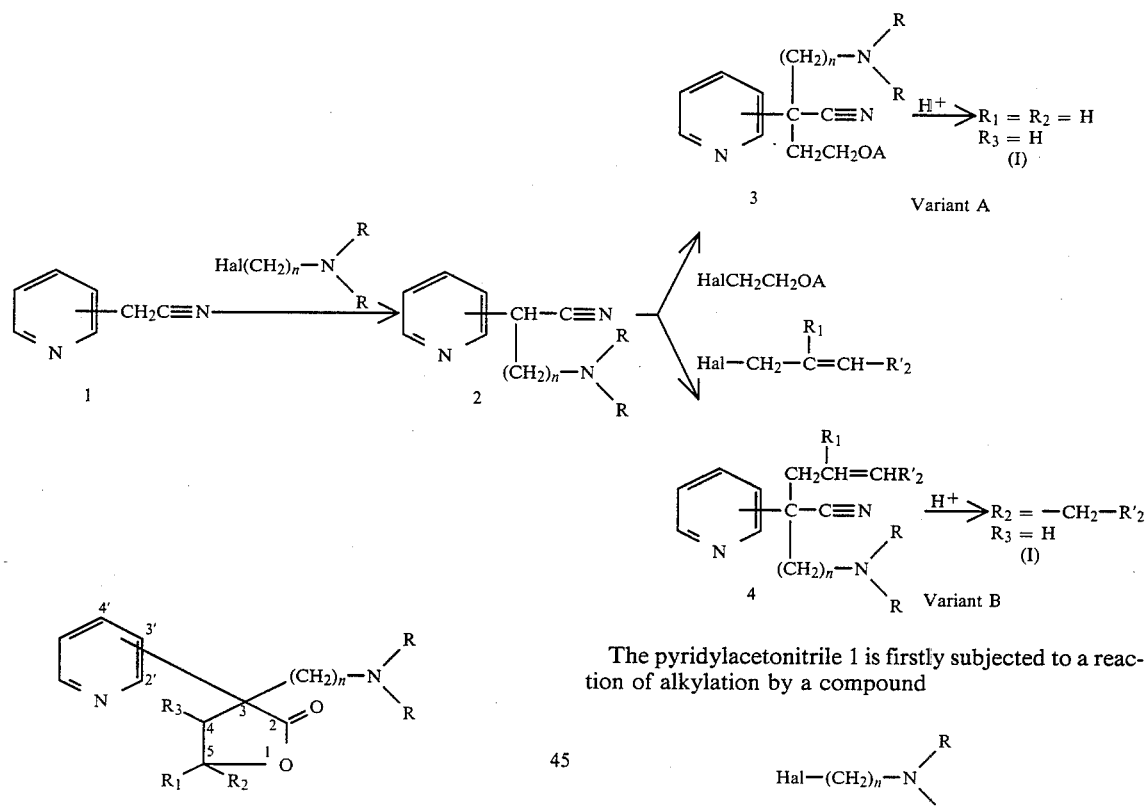

The pyridylacetonitrile 1 is firstly subjected to a reaction of alkylation by a compound $$Hal-(CH_2)_n-N\begin{matrix}R\\R\end{matrix}$$

(Hal representing a halogen), in the presence of an organic or inorganic base to lead to compound 2. From the latter, two variants are possible:

Variant A

Compound 2 is again substituted by a compound Hal—CH₂CH₂OA in which Hal represents a halogen and A represents a group protecting the hydroxyl function which is easy to eliminate in acid medium and in particular a tetrahydropyrannyl group.

Operation is carried out in an inert solvent such as a benzene hydrocarbon in the presence of sodium hydride, at a temperature of between 80° and 120° C.

Compound 3 thus obtained is treated by a concentrated inorganic acid such as 85% phosphoric acid to lead to compound (I) where R₁=R₂=H.

Variant B

Compound 2 is again substituted by an unsaturated derivative

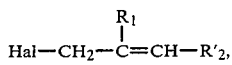

in which Hal represents a halogen and $R'_2$ represents hydrogen or an alkyl group with 1 or 2 carbon atoms, or $R_1+R_2$ represents a group $(CH_2)_{m'}$ with $m'=3$ or 4.

Reaction takes place within a solvent such as dimethyformamide in the presence of sodium amide at a temperature of between 20° and 80° C.

Compound 4 thus obtained is treated by a concentrated inorganic acid and in particular by concentrated sulfuric acid to lead to compound (I) in which substituent $R_2$ represents $CH_2R'_2$.

When $R_1$ represents H and $R_2$ and $R_3$ represent, together, $(CH_2)_p$, compounds (I) may be obtained in accordance with the following reaction diagram:

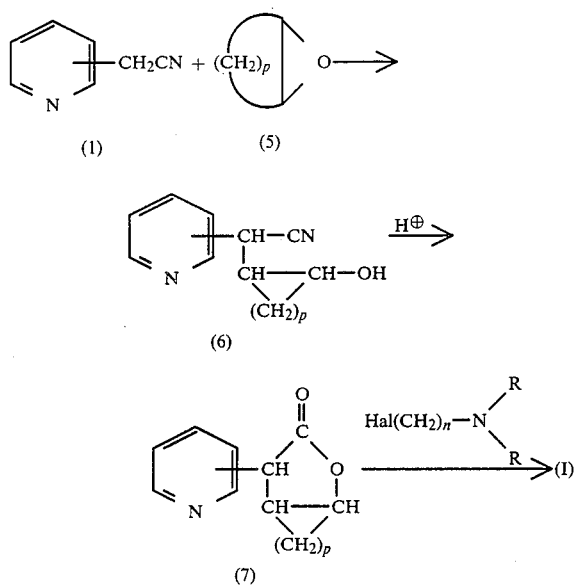

The opening of epoxide 5 by the anion of the pyridylacetonitrile (1) leads to hydroxynitrile (6).

To obtain the pyridylacetonitrile anion, lithium diisopropylamidine is used (prepared in situ by the action of diisopropylamine on butyllithium) within an inert solvent such as tetrahydrofuran and operating at low temperature ($-6°$ to $-80°$ C.). Hydroxynitrile 6 leads to the ketone 7 by hydrolysis in acid medium and to this end a concentrated inorganic acid such as 85% phosphoric acid is preferably used. Finally, compound (I) where $R_1=H$ and $R_2+R_3=(CH_2)_p$ is obtained by substitution of compound 7 with a derivative of formula

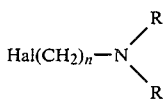

(in which Hal is a halogen) in the presence of a sodation agent such as sodium hydride within a solvent such as tetrahydrofuran.

The salts of compounds (I) are obtained by the conventional methods of salification.

When $R_1$ and $R_2$ are different, products (I) exist in the form of diastereoisomers. The process according to the invention leads to a mixture of diastereoisomers. This mixture may be used as such or separated into its constituents by the conventional methods and, in particular, by chromatography.

The following examples, which are in no way limiting, are given by way of illustration for the preparation of the compounds according to the invention.

EXAMPLE 1

3-(2-diisopropylamino ethyl) 3-(2-pyridyl) γ-butyrolacetone, phosphate (SR 41340)

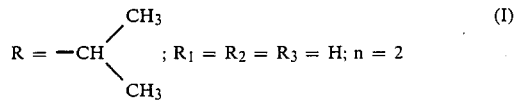

(a) 4-diisopropylamino 2-(2-pyridyl)butyronitrile 8 g of 2-pyridyl acetonitrile, 8.8 g of 1-chloro 2-diisopropylamino ethane and 0.27 g of benzyltrimethylammonium chloride are mixed, then, maintaining the temperature below 35° C., 35 ml of 50% sodium hydroxide solution are added. The mixture is heated to 35° C. for 5 hours. After cooling, it is diluted with water and extracted with ether. The organic phase is separated and dried over sodium sulfate, then the solvent is evaporated to dryness.

By distilling the residue, a yellow oil (9.36 g) is obtained; b.p./$_{0.06}$ mm Hg: 132°-134° C.

(b) 2-(2-diisopropylamino ethyl) 2-(2-pyridyl) 4-(2-tetrahydropyranyloxy)butyronitrile The mixture of 9.3 g of the nitrile obtained above, 7.5 g of 1-chloro 2-(2-tetrahydropyranyloxy)ethane and 1.75 g of sodium hydride in 200 ml of toluene is taken to reflux for 18 hours. After cooling, water is added, then the organic phase is decanted. The substance is dried over sodium sulfate and the solvent is evaporated to dryness.

An oil is obtained (14 g) used as such for the following operation.

(c) SR 41340

The product obtained in paragraph (b) is dissolved in 70 ml of 85% phosphoric acid and the mixture is heated to 90°-100° C. for 1 hour. The mixture is poured over ice and extracted with ether. The organic phase is separated and the aqueous phase is rendered alkaline with a solution of potassium carbonate. It is extracted again with ether and the organic extracts are collected. The substance is dried over sodium sulfate, then the solvent is evaporated to dryness and the residue is distilled under reduced pressure.

An oil is obtained (7.5 g); b.p./$_{0.1 \ mm \ Hg}$: 149°-152° C.

Phosphate 5.5 g of the above product are dissolved in 50 ml of ethanol and 2.18 g of an 85% phosphoric acid solution are added. Evaporation takes place, the residue is taken up in ether and left to crystallize. The solid is drained and washed with ether.

Weight: 5.95 g; m.p.: 107°-109° C.

EXAMPLE 2

5-cyclohexanespiro 3-(2-diisopropylamino ethyl) 3-(2-pyridyl) γ-butyrolactone (SR 41412)

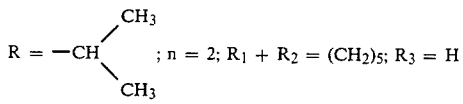

R = —CH(CH₃)(CH₃) ; n = 2; R₁ + R₂ = (CH₂)₅; R₃ = H    (I)

(a) 2-(1-cyclohexenyl methyl) 4-diisopropylamino 2-(2-pyridyl)butyronitrile

In a three-necked bottle, 1.45 g of sodium hydride and 20 ml of dimethylformamide are introduced in an atmosphere of nitrogen. The solution of 12.25 g of 4-diisopropylamine 2-(2-pyridyl)butyronitrile (Example 1(a)) in 20 ml of dimethylformamide is added drop by drop, then, after the end of introduction, the mixture is stirred for 1 hour at ambient temperature.

9.6 g of 1-bromomethyl cyclohexene dissolved in 20 ml of dimethylformamide are then added and the mixture is stirred again for 2 hours at ambient temperature. The solvent is evaporated in vacuo and the residue is taken up in water and ether. The organic layer is separated and the aqueous phase is re-extracted with ether. The ethereal extracts are collected, dried over sodium sulfate and the solvent is evaporated to dryness.

18 g of crude product are obtained, used as such for the following step.

(b) SR 41412

The compound obtained hereinabove is dissolved in 150 ml of 85% phosphoric acid and the mixture is heated to 130° C. for 3 hours.

The reaction mixture is poured over ice and ether is added, then the aqueous phase is rendered alkaline by a 40% sodium hydroxide solution with cooling so that the temperature remains less than 20° C.

The ethereal layer is separated and re-extracted with ether. The ethereal extracts are dried over sodium sulfate and the solvent is evaporated to dryness.

The residue (8.7 g) is chromatographed over a column of alumina. By eluting with the pentane-ethyl acetate (97-3) vol/vol mixture, 3.1 g of the expected product are obtained, which crystallize. m.p.: 42°–44° C.

EXAMPLE 3

3-(2-diisopropylamino ethyl) 5-methyl 3-(2-pyridyl) γ-butyrolactone, phosphate (SR 41653)

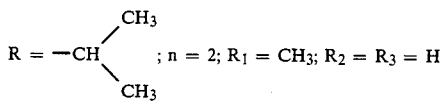

R = —CH(CH₃)(CH₃) ; n = 2; R₁ = CH₃; R₂ = R₃ = H    (I)

Mixture of the diastereoisomers.

Operation is carried out as in Example 2 from the same starting product but by replacing in step (a) 1-bromomethyl cyclohexene by an equivalent quantity of allyl bromide. Cyclization is effected as in Example 2(b) by heating to 150° C. for 6 hours. The crude product thus obtained is distilled under reduced pressure.

b.p./$_{0.15\ mm\ Hg}$: 120°–124° C.

The phosphate is prepared as in Example 1(c). m.p.: 157°–159° C.

EXAMPLE 4

5,5-dimethyl 3-(2-di-sec-butylamino ethyl) 3-(2-pyridyl) γ-butyrolactone (SR 41652)

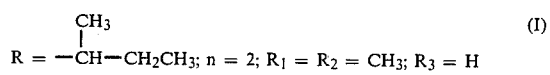

R = —CH(CH₃)—CH₂CH₃; n = 2; R₁ = R₂ = CH₃; R₃ = H    (I)

The starting product is prepared as in Example 1(a), replacing 1-chloro 2-diisopropylamino ethane by an equivalent quantity of 1-chloro 2-di-sec-butylamino ethane. b.p./$_{0.1\ mm\ Hg}$: 120°–125° C.

From this product, operation is carried out as in Example 2(a), replacing the 1-bromomethyl cyclohexene by an equivalent quantity of 3-chloro 2-methyl propene.

The crude product thus obtained is cyclized as in Example 2(b). After chromatography over a column of alumina, eluting with the pentane-ethyl acetate (95-5) vol/vol mixture, the expected product is obtained. m.p.: 67°–68° C.

EXAMPLE 5

3-(2-diisopropylamino ethyl) 5,5-dimethyl 3-(2-pyridyl) γ-butyrolactone, SR 41098

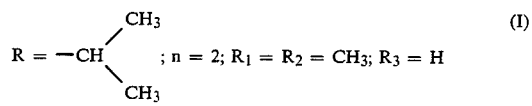

R = —CH(CH₃)(CH₃) ; n = 2; R₁ = R₂ = CH₃; R₃ = H    (I)

From the starting product of Example 1(a), operation is carried out as in Example 4 with 3-chloro 2-methyl propene. The crude product thus obtained is cyclized by heating to 50° C. for 30 mins. with concentrated sulfuric acid (d: 1.83). Treatment is as described in Example 2(b) and, after chromatography over alumina, eluting with the pentane-ethyl acetate (90-10) vol/vol mixture, the expected product is obtained. m.p.: 58°–59° C.

EXAMPLES 6 to 21

By operating as in Example 1(a), but by varying the halogen derivative used, various substituted nitriles 2 are obtained. By action thereon of a suitably selected unsaturated derivative and by operating as in Examples 2, 4 and 5, corresponding compounds 4 are obtained which are directly cyclized into compound (I) either by phosphoric acid according to Example 4 or by sulfuric acid according to Example 5. Products (I) thus prepared are collected in Table I hereinafter.

TABLE 1

[Structure: pyridine ring (positions 2, 3, 4 shown, N in ring) attached at position 2 to a carbon bearing (CH₂)ₙ-NR₂ group and C(=O)-O group; with R₃ on adjacent carbon and R₁, R₂ on terminal carbon]

| Example no | no code product | Position substitution pyridine | n | -N(R)(R) | R₁ | R₂ | R₃ | Cyclization | Base or salt m.p., °C. (solvent) |
|---|---|---|---|---|---|---|---|---|---|
| 6 | SR 41696 | 2 | 2 | cis-2,6-dimethylpiperidino (CH₃, cis-N, CH₃) | —CH₃ | —CH₃ | H | SO₄H₂ | Base m.p.: 58–59 |
| 7 | SR 41816 | 2 | 3 | —N[CH—(CH₃)₂]₂ | —CH₃ | —CH₃ | H | SO₄H | Dihydrochloride 1H₂O m.p.: 158–160 (isopropanol) |
| 8 | SR 41913 | 2 | 2 | 2,6-dimethylmorpholino (CH₃, —N, O, CH₃) | —CH₂ | —CH₃ | H | SO₄H₂ | Dihydrochloride m.p.: 201–202 (acetone) |
| 9 | SR 41914 | 2 | 2 | —N(C₂H₅)₂ | —CH₃ | —CH₃ | H | PO₄H₃ | Dihydrochloride 0,5H₂O m.p.: 140–142 (isopropanol) |
| 10 | SR 41941 | 2 | 2 | —N(C₃H₇)₂ | —CH₃ | —CH₃ | H | SO₄H₂ | Oxalate m.p.: 103–105 (acetone) |
| 11 | SR 41942 | 2 | 2 | —N[CH(CH₃)₂]₂ | —C₂H₅ | —C₂H₅ | H | PO₄H₃ | Oxalate m.p.: 128–130 (ether) |
| 12 | SR 41943 | 2 | 2 | morpholino (—N, O) | —CH₃ | —CH₃ | H | PO₄H₃ | Oxalate m.p.: 188–189 (ethanol) |
| 13 | SR 41944 | 2 | 2 | piperidino (—N) | —CH₃ | —CH₃ | H | PO₄H₃ | Base m.p.: 55–57 (hexane) |
| 14 | SR 42167 | 2 | 2 | cis-2,6-dimethylpiperidino (CH₃, cis-N, CH₃) | (CH₂)₅ | | H | PO₄H₃ | hydrochloride 0.75H₂O m.p.: 135–137 (butanone-2) |
| 15 | SR 42180 | 2 | 2 | 2,2,6,6-tetramethylpiperidino (H₃C, CH₃, —N, H₃C, CH₃) | —CH₃ | —CH₃ | H | PO₄H₃ | Base m.p.: 87–88 (ethanol-water) |

TABLE 1-continued

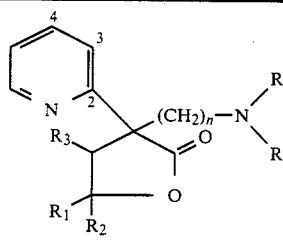

| Example no | no code product | Position substitution pyridine | n | —N(R)(R) | R₁ | R₂ | R₃ | Cyclization | Base or salt m.p., °C. (solvent) |
|---|---|---|---|---|---|---|---|---|---|
| 16 | SR 42205 | 2 | 2 | —N[CH(CH₃)₂]₂ | —C₃H₇ | —C₃H₇ | H | PO₄H₃ | Oxalate m.p.: 121–123 (acetone) |
| 17 | SR 42206 | 3 | 2 | cis-2,6-dimethylpiperidino | —CH₃ | —CH₃ | H | PO₄H₃ | Base (liquid) |
| 18 | SR 42298 | 2 | 2 | " | —C₂H₅ | —C₂H₅ | H | PO₄H₃ | Oxalate, 0.75H₂O m.p.: 80–82 (ethyl acetate) |
| 19 | SR 42408 | 2 | 2 | " | —C₃H₇ | —C₃H₇ | H | PO₄H₃ | Dihydrochloride m.p.: 189–190 (isopropanol) |
| 20 | SR 42435 | 2 | 3 | " | —CH₃ | —CH₃ | H | PO₄H₃ | Phosphate m.p.: 165–167 (isopropanol) |
| 21 | SR 42483 | 2 | 2 | trans-2,6-dimethylpiperidino | —CH₃ | —CH₃ | H | SO₄H₂ | Base (liquid) |

EXAMPLE 22

3-[2-(2,6-cis-dimethyl piperidino)ethyl] 3-(2-pyridyl)-hexahydro transbenzo-furanone-2(3H) (SR 42455)

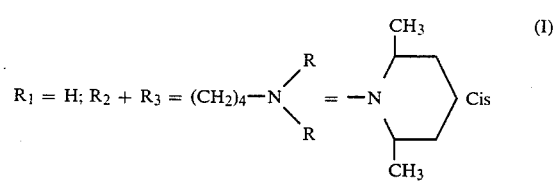

(a) α-(trans-hydroxy-2 cyclohexyl) 2-pyridyl acetonitrile

To the mixture of 45.45 g of diisopropylamine and 200 ml of anhydrous tetrahydrofuran cooled to −20° C. are added, in an atmosphere of nitrogen and with stirring, 300 ml of a 1.6M solution of butyllithium in hexane. The mixture is then cooled to −70° C., then the solution of 53.1 g of 2-pyridyl acetonitrile in 200 ml of anhydrous tetrahydrofuran is added. The mixture is stirred for 15 minutes at a temperature less than or equal to −70° C., then the solution of 48.5 g of epoxycyclohexane in 200 ml of anhydrous tetrahydrofuran is added at the same temperature. The temperature is allowed to rise up to ambient temperature (about 20° C.) and the mixture is stirred for 15 hours at this temperature.

The mixture is cooled by an ice bath and 300 ml of water are added. The organic phase is decanted then the aqueous phase is re-extracted twice with ether.

The organic phases are collected, washed twice with a saturated solution of sodium chloride then the solution is dried over sodium sulfate. The solvents are evaporated to dryness and the residue is crystallized in isopropanol.

74.6 g of the expected product are obtained. m.p.: 110°–112° C.

(b) 3-(2-Pyridyl)hexahydro-trans-benzofuranone-2 (3H)

The mixture of 32.4 g of the product obtained above and 160 ml of 85% phosphoric acid is heated to 90° C. for 30 minutes. The reaction mixture is poured over ice then rendered alkaline by adding a 30% sodium hydroxide solution, maintaining the temperature below 25° C.

The mixture is extracted with ethyl acetate and the solution is dried over sodium sulfate. The solvent is evaporated to dryness and the solid residue is taken up in isopropyl ether. The solid is drained and the expected product is obtained (31 g). m.p.: 124°–125° C.

(c) SR 42455

100 ml of anhydrous tetrahydrofuran and 2.5 g of a 55% suspension in the oil of sodium hydride are introduced in a flask in an atmosphere of nitrogen. The mixture is heated to reflux then the solution in 250 ml of anhydrous tetrahydrofuran of 10.85 g of the product obtained above and 9.7 g of 1-(2-chloro ethyl) 2,6-cis-dimethyl piperidine is added drop by drop. After the end of the addition, reflux is maintained for 1 hour then the tetrahydrofuran is evaporated. The residue is taken up in water and extracted with ether. The solution is dried over sodium sulfate then the solvent is evaporated and the oily residue is chromatographed over a column of alumina.

By eluting with a pentane-ethyl acetate (95-5) vol/vol mixture, an oil is obtained (6.7 g).

Pentane is added and the mixture is left to crystallize slowly at 0° C. The solid is drained and washed with a little pentane cooled to 0° C. Crystals are finally obtained (3.5 g). m.p.: 81°-82° C.

The products of the invention have been studied in pharmacology, particularly with a view to demonstrating their anti-arrythmic properties.

Protocol

The anti-arrythmic power of these molecules was assessed on an animal model of ventricular arrhythmia.

Mongrel dogs are anaesthetized then subjected to the positioning, by retrograde catherism, of a metal turn in the coronary bed. At the same time, a frequency modulator micro-emitter is fixed to the animal's back and connected to two precordial electrodes.

The animal, returned to its cage, then shows a progressive thrombosis of the anterior interventricular artery. A localized, transmural myocardial infarction is thus constituted, generating an abnormal but repetitive electrical activity: ventricular tachycardia.

In this state, 24 hours after the turn has been positioned, the drugs are administered per os and the telemetered system enables the development of the arrhythmia of the alert dog to be followed in real time.

The systolic, sinusal and pathological complexes are permanently metered by electronic processes. The quality and duration of action of the product may thus be quantified. The animal's behaviour is observed.

Results

A product is considered active if it eliminates at least 60% of the abnormal complexes or if it induces a sinusal rhythm.

The results obtained with various products of the invention are shown in Table 2.

TABLE 2

| Product SR Code No. | Dose mg/kg per os | Number of animals | Duration of action |
|---|---|---|---|
| 41098 | 50 | 2 | 3 hours |
| 41412 | 50 | 1 | 1 hour |
| 41652 | 50 | 1 | 1 hour 50. |
| 41653 | 50 | 1 | 1 hour 25. |
| 41696 | 20 | 1 | longer than 24 hrs. |
|  | 5 | 1 | 3 hrs. 30. |
|  | 3 | 1 | 2 hours |
| 41816 | 50 | 2 | longer than 24 hrs. |
| 41913 | 50 | 1 | longer than 24 hrs. |
| 41942 | 50 | 1 | longer than 24 hrs. |
| 42180 | 50 | 1 | 8 hours |

These results show that the products according to the invention have a considerable activity on the arrhythmia.

Furthermore, the compounds according to the invention are relatively non-toxic and, in particular, present no sign of toxicity at doses where they manifest their anti-arrhythmic activity.

Consequently, products (I) may be used in human therapeutics as protector of the myocardium for correcting disorders of the ventricular rhythm of ischemic origin.

The products may be presented in the galenic forms for administration by the oral route (tables, capsules, . . . ) and for administration by the parenteral route (injectable ampoules).

The dose necessary for restoring the sinusal rhythm in man is included between about 5 and 150 mg by the intravenous route and between about 40 and 800 mg by the oral route, per day.

The following galenic preparation is indicated by way of example:

| Compounds | |
|---|---|
| SR 41696 | 0.200 g |
| Microcrystalline cellulose | 0.140 g |
| Lactose | 0.140 g |
| Magnesium stearate | 0.020 g |
| | 0.500 g |

What is claimed is:

1. Derivatives of γ-butyrolactone of formula:

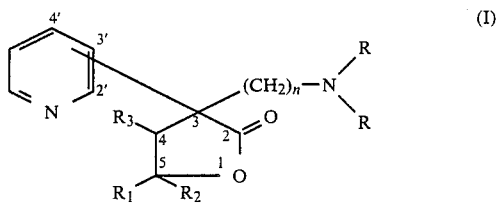

in which:

R represents a straight or branched alkyl group having from 2 to 5 atoms of carbon, or the group

represents a morpholino or piperidino group possibly substituted by 1 to 4 methyl groups;

n=2 or 3;

$R_1$ and $R_2$ considered independently each represent hydrogen or a lower alkyl group (1 to 4 carbon atoms) or $R_1$ and $R_2$ taken together represent a $(CH_2)_m$ group where m=4 or 5, and $R_3$ is H or $R_1$ is H and $R_2$ and $R_3$ taken together represent $(CH_2)_p$ where p is 3 or 4 the butyrolactone cycle being attached to the pyridyl cycle in 2', 3' or 4' position;

and the salts, isomers and mixtures of isomers of said products.

2. A derivative according to claim 1, wherein the group

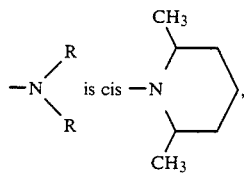

n is 2, R₁ and R₂ each represent —CH₃, R₃ is H and the position substitution on the pyridyl cycle is at the 2' position.

3. A derivative according to claim 1, wherein the group

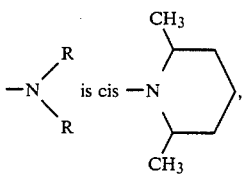

n is 2, R₁ and R₂ together represent (CH₂)₅, R₃ is H, and the position substitution on the pyridyl cycle is at the 2' position.

4. A derivative according to claim 1, wherein the group

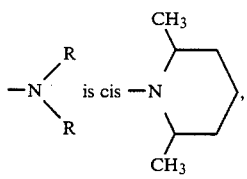

n is 2, R₁ and R₂ each represent —CH₃ and R₃ is H.

5. A derivative according to claim 1, wherein the group

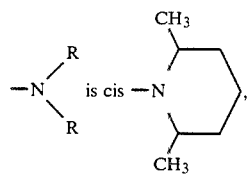

n is 2, R₁ and R₂ each represent —C₂H₅, R₃ is H and the position substitution on the pyridyl cycle is at the 2' position.

6. A derivative according to claim 3, which is in the form of a hydrochloride salt.

7. A derivative according to claim 4, wherein the position substitution on the pyridyl cycle is at the 3' position.

8. A derivative according to claim 5 which is in the form of a dihydrochloride salt.

9. The derivatives according to claim 1, wherein the group

represents a cis-2,6-dimethyl piperidino group.

10. A pharmaceutical composition having an amount of the compound of claim 1 which is effective to produce a myocardium-protecting effect, and a pharmaceutical carrier.

11. A pharmaceutical composition according to claim 10 wherein the myocardium-protecting effective amount is from 5 to 800 mg.

* * * * *